United States Patent
Vesely

(10) Patent No.: US 7,825,092 B2
(45) Date of Patent: Nov. 2, 2010

(54) DENDROASPIS NATRIURETIC PEPTIDE FOR TREATMENT OF CANCER

(75) Inventor: David L. Vesely, Tampa, FL (US)

(73) Assignees: University of South Florida, Tampa, FL (US); United States Department of Veteran Affairs, Washington, DC (US)

( * ) Notice: Subject to any disclaimer, the term of this patent is extended or adjusted under 35 U.S.C. 154(b) by 0 days.

(21) Appl. No.: 11/833,757

(22) Filed: Aug. 3, 2007

(65) Prior Publication Data

US 2008/0039394 A1 Feb. 14, 2008

Related U.S. Application Data

(60) Provisional application No. 60/821,760, filed on Aug. 8, 2006.

(51) Int. Cl.
*A61K 38/16* (2006.01)
*A61K 38/17* (2006.01)
(52) U.S. Cl. .............................. 514/12; 514/2
(58) Field of Classification Search ....................... None
See application file for complete search history.

(56) References Cited

U.S. PATENT DOCUMENTS

| 4,753,945 | A | 6/1988 | Gilbard et al. |
|---|---|---|---|
| 5,545,614 | A | 8/1996 | Stamler et al. |
| 5,602,143 | A | 2/1997 | Krauss |
| 5,625,056 | A | 4/1997 | Genieser et al. |
| 5,665,861 | A | 9/1997 | Forssmann et al. |
| 5,858,694 | A | 1/1999 | Piazza et al. |
| 6,943,147 | B2 * | 9/2005 | Vesely .......................... 514/12 |
| 7,488,713 | B2 * | 2/2009 | Vesely .......................... 514/12 |
| 2002/0094326 | A1 | 7/2002 | Donahue et al. |
| 2003/0105000 | A1 | 6/2003 | Pero et al. |
| 2003/0215528 | A1 | 11/2003 | Graham et al. |
| 2004/0229784 | A1 | 11/2004 | Vesely |
| 2004/0258687 | A1 | 12/2004 | Waldman et al. |
| 2005/0176641 | A1 | 8/2005 | Bakis et al. |
| 2005/0209139 | A1 | 9/2005 | Vesely |
| 2005/0272650 | A1 | 12/2005 | Mohapatra |
| 2006/0014689 | A1 | 1/2006 | Vesely |
| 2006/0019256 | A1 | 1/2006 | Clarke et al. |
| 2006/0276382 | A1 | 12/2006 | Mohapatra |
| 2007/0265204 | A1 | 11/2007 | Mohapatra et al. |
| 2008/0070858 | A1 | 3/2008 | Mohapatra |
| 2008/0214437 | A1 | 9/2008 | Mohapatra et al. |
| 2009/0062206 | A1 | 3/2009 | Vesely |
| 2009/0170196 | A1 | 7/2009 | Vesely |
| 2009/0176706 | A1 | 7/2009 | Mohapatra |

FOREIGN PATENT DOCUMENTS

| WO | WO 2004/022003 A3 | 3/2004 |
|---|---|---|
| WO | WO 2004/083236 A3 | 9/2004 |
| WO | WO 2005/094420 A3 | 10/2005 |
| WO | WO 2006/026536 A3 | 3/2006 |
| WO | WO 2007/127487 A3 | 11/2007 |
| WO | WO 2007/130672 A3 | 11/2007 |
| WO | WO 2009/073527 A3 | 6/2009 |

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Gura (Science, v278, 1997, pp. 1041-1042).*
Bellone et al. . (Immunology Today, v20 (10), 1999, pp. 457-462).*
Gaiger et al. (Blood, vol. 96, No. 4, Aug. 2000, pp. 1480-1489).*
Daggubati, S., Parks, J.R., Overton, R.M., Cintron, G., Schocken, D.D., and Vesely, D.L. (1997) Adrenomedullin, endothelin, neuropeptide Y, atrial, brain, and C-natriuretic prohormone peptides compared as early heart failure indicators. Cardiovascular Res. 36, 246-255.
De Palo, E.F., Woloszczuk, W., Meneghetti, M., DePalo, CB., Nielsen, H.B., and Secher, N.H. (2000) Circulating immunoreactive proANP (1-30) and proANP (31-67) in sedentary subjects and athletes. Clin. Chem. 46, 843-847.
Fisher, E.R., Palekar, A., and Paulson, J.D. (1978) Comparative histopathologic, histochemical, electron microscopy and tissue culture studies of bronchial carcinoids and oat cell carcinomas of lung. Am. J. Clin. Pathol. 69, 165-172.
Franz, M., Woloszczuk, W., and Horl, W.H. (2000 ) N-terminal fragments of the proatrial natriuretic peptide in patients before and after hemodialysis treatment. Kidney Int. 58, 374-378.
Franz, M., Woloszczuk, W., and Horl, W.H. (2001 ) Plasma concentration and urinary excretion of N-terminal proatrial natriuretic peptides in patients with kidney diseases. Kidney Int. 59, 1928-1934.
Friedman, H.S., and Bigner, D.D. (2005) Glioblastoma multiforme and the epidermal growth factor receptor. N. Eng. J. Med. 353, 1997-1999.

(Continued)

*Primary Examiner*—Christine J Saoud
(74) *Attorney, Agent, or Firm*—Saliwanchik, Lloyd & Saliwanchik

(57) ABSTRACT

Disclosed is a method of inhibiting the growth of a cancer cell using Dendroaspis natriuretic peptide (DNP), isolated from the Green Mamba snake venom with similar structure to ANP, with or without four cardiac natriuretic peptides i.e., atrial natriuretic peptide (ANP), vessel dilator, long acting natriuretic peptide (LANP), and kaliuretic peptide. Dose-response curves revealed a significant (p<0.0001) decrease in human glioblastoma cells with each ten-fold increase in concentration from 1 μM to 100 μM of four of the cardiac peptide hormones. There was an 75%, 68%, 67%, and 65% elimination within 24 hours of glioblastoma cells secondary to vessel dilator, kaliuretic peptide, ANP, and LANP, respectively (p<0.0001) while DNP had no significant effect at 1 μM (2% decrease), and 10 μM (7%), but 100 μM caused a (17%) decrease (p<0.05). Three days after treatment with these peptide hormones, the cancer cells began to proliferate again. These same hormones decreased DNA synthesis from 65% to 87% (p<0.00001).

17 Claims, 5 Drawing Sheets

OTHER PUBLICATIONS

Gower, W.R., Jr., Vesely, B.A., Alli, A.A., and Vesely, D.L. (2005) Four peptides decrease human colon adenocarcinoma cell number and DNA synthesis via guanosine 3', 5'-cyclic monophosphate. Int J Gastrointestinal Cancer 36, 77-88.

Gratzner, H.G. (1982) Monoclonal antibody to 5-bromo-ad 5-Iodo-deoxyuridine: A new reagent for detection of DNA replication. Science 18, 474-475.

Hunter, E.F.M., Kelly, P.A., Prowse, C., Woods, F.J., and Lowry, P.J. (1998) Analysis of peptides derived from proatrial natriuretic peptide that circulate in man and increase in heart disease. Scan. J. Clin. Lab. Invest. 58, 205-216.

Jemal, A., Murray, T., Ward, E., Samuels, A., Tiwari, R.C., Ghafoor, A., Feuer, E.J., and Thun, M.J. (2005) Cancer Statistics. CA Cancer J. Clin. 55, 10-30.

Mellinghoff, I.K., Wang, M.Y., Vivanco, I., Haas-Kogan, D.A., Zhu, S, Dia, E.Q., Lu, K.V., Yoshimoto, K., Huang, J.H.Y., Chute, D.J., Riggs, B.L., Horvath, S., Liau, L.M., Cavenee, W.K., Rao, P.N., Beroukhim, R., Peck, T.C., Lee, J.C., Sellers, W.R., Stokoe, D., Prados, M., Cloughesy, T.F., Sawyers, C.L., and Mischel, P.S. (2005) Molecular determinants of the response of glioblastomas to EGFR kinase inhibitors. N. Engl J. Med. 353, 2012-2024.

Morstyn, G., Pyke, K, Gardner, J., Ashcroft, R., deFazio, A., and Bhathal, P. (1986) Immunohistocemical identification of proliferatory cells in organ culture using bromodeoxyuridine and a monoclonal antibody. J. Histochem. Cytochem. 34, 697-701.

Ropper, A.H., and Brown, R.H. (Eds.) (2005) Intracranial neoplasms and paraneoplastic disorders. In: Adams and Victor's Principles of Neurology, 8th Edition. New York: McGraw-Hill, pp. 546-591.

Salani, D., Taraboletti, G., Rosano, L., Di Castro, V., Borsotti, P, Giavazzi, R., and Bagnato, A. (2000) Endothelin-1 induces an angiogenic phenotype in cultured endothelial cells and stimulates neovascularization in vivo. Am. J. Pathol. 157, 1703-1711.

Schweitz, H., Vigne, P., Moinier, D., Frelin, C., and Lazdunski, M. (1992) A new member of the natriuretic peptide family is present in the venom of the Green Mamba (*Dendroaspis augusticeps*). J. Biol. Chem. 267, 13928-13932.

Senger, D., Cairncross, J.G., and Forsyth, P.A. (2003) Long-term survivors of glioblastoma: Statistical aberration or important unrecognized molecular subtype? Cancer J. 9, 214-221.

Van Meir, E.G., Polverini, P.J., Chazin, V.R., Huang, S., de Tribolet, N., and Cavenee, W.K. (1994) Release of an inhibitor of angiogenesis upon induction of wild type p53 expression in glioblastoma cells. Nat. Genet. 8, 171-176.

Vesely, B.A., Alli, A.A., Song, S., Gower, W.R., Jr., Sanchez-Ramos, J., and Vesely, D.L. (2005a) Four peptide hormones specific decrease (up to 97%) of human prostate carcinoma cells. Eur. J. Clin. Invest. 35, 700-710.

Vesely, B.A., Fitz, S.R., Gower, W.R., Jr., and Vesely, D.L. (2006) Vessel dilator: Most potent of the atrial natriuretic peptides in decreasing the number and DNA synthesis of squamous lung cancer cells. Cancer Lett. 232, 226-231.

Vesely, B.A., McAfee, Q., Gower, W.R., Jr., and Vesely, D.L. (2003) Four peptides decrease the number of human pancreatic adenocarcinoma cells. Eur. J. Clin. Invest. 33, 998-1005.

[00069] Vesely, B.A., Song, S., Sanchez-Ramos, J., Fitz, S.R., Solivan, S.M., Gower, W.R., Jr., and Vesely, D.L. (2005c) Four peptide hormones decrease the number of human breast adenocarcinoma cells. Eur. J. Clin. Invest. 35, 60-69.

Vesely, D.L., Clark, L.C., Garces, A.H., McAfee, Q.W., Soto, J., and Gower, W.R., Jr. (2004) Novel therapeutic approach for cancer using four cardiovascular hormones. Eur. J. Clin. Invest. 34, 674-682.

Vesely, B.A., Song, S., Sanchez-Ramos, J., Fitz, S.R., Alli, A., Solivan, S.M., Gower, W.R., Jr., and Vesely, D.L.(2005b) Five cardiac hormones decrease the number of human small-cell cancer cells. Eur. J. Clin. Invest. 35, 388-398.

Vesely, D.L., Dietz, J.R., Parks, J.R., Baig, M., McCormick, M.T., Cintron, G., and Schocken, D.D. (1998) Vessel dilator enhances sodium and water excretion and has beneficial hemodynamic effects in persons with congestive heart failure. Circulation 98, 323-329.

Vesely, D.L., Douglass, M.A., Dietz, J.R., Giordano, A.T., McCormick, M.T., Rodriguez-Paz, G., and Schocken, D.D. (1994a) Negative feedback of atrial natriuretic peptides. J Clin Endocrinol. Metab. 78, 1128-1134.

Vesely, D.L., Douglass, M.A., Dietz, J.R., Gower, W.R., McCormick, M.T., Rodriguez-Paz, G., and Schocken, D.D. (1994b) Three peptides from the atrial natriuretic factor prohormone amino terminus lower blood pressure and produce diuresis, natriuresis and/or kaliuresis in humans. Circulation 90, 1129-1140.

Vesely, D.L., Norsk, P., Winters, C.J., Rico, D.M., Sallman, A.L., and Epstein, M. (1989) Increased release of the N-terminal and C-terminal portions of the prohormone of atrial natriuretic factor during immersion-induced central hypervolemia in normal humans. Proc. Soc. Exp. Biol. Med. 192, 230-235.

Weller, M., Rieger, J., Grimmel, C., Van Meir, E.G., De Tribolet, N., Krajewski, S., Reed, J.C., von Deimling, A., and Dichgans, J. (1998) Prediciting chemoresistance in human malignant glioma cells: The role of molecular genetic analyses. Int. J. Cancer 79, 640-644.

Winters, C.J., Sallman, A.L., Baker, B.J., Meadows, J., Rico, D.M., and Vesely, D.L. (1989 ) The N-terminus and a 4000 molecular weight peptide from the mid portion of the N-terminus of the atrial natriuretic factor prohormone each circulate in humans and increase in congestive heart failure. Circulation 80, 438-449.

Yu, C.C.W., Woods, A.L., and Levison, D.A. (1992) The assessment of cellular proliferation by immunohistochemistry: a review of currently available methods and their applications. Histochemical J. 24, 121-131.

U.S. Appl. No. 12/346,192, filed Dec. 30, 2008, Vesely.

Pan, E. et al. "Central Nervous System: Primary Neoplasms of the Central Nervous System" In: Kufe, D.W., Pollock, R.F., Weichselbaum, R.R., Bast, R.C., Jr., Gensler, I.S., Holland, J.F., and Frei, E., III (Eds.), *Cancer Medicine*, 6$^{th}$ Edition. 2003, pp. 1193-1226, London: BC Decker.

Vesely, B.A. et al. "Primary Malignant Tumors of the Heart: Four Cardiovascular Hormones Decrease the Number and DNA Synthesis of Human Angiosarcoma Cells" *Cardiology*, 2006, 105:226-233.

Vesely, B.A. et al. "Four cardiac hormones eliminate 4-fold more human glioblastoma cells than the green mamba snake peptide" *Cancer Letters*, 2007, 254:94-101.

ATCC No. CCL-248 (T84, 1984).

Benjamin, B.A. et al. "Effect of proANF-(31-67) on sodium excretion in conscious monkeys" *Am J Physiol Regul Integr Comp Physiol*, 1995, pp. R1351-R1355, vol. 269, abstract.

Buskens, C. et al. "Adenocarcinomas of the Gastro-Esophageal Junction: A Comparative Study of the Gastric Cardia and the Esophagus with Respect to Cyclooxygenase-2 Expression" *Digestive Disease Week Abstracts and Itinerary Planner*, 2003, Abstract No. 850.

Capizzi, R.L. "Molecular and Cellular Biology of Cancer" In: Internal Medicine, 4th Edition, Ed. Jay Stein, Elsevier Science, 1994, pp. 707-729.

Carter, S.K. et al. "Chemotheraphy of Cancer" Second Edition, John Wiley & Sons: New York, 1981, Appendix C.

Chow, W.H. et al. "Rising Incidence of Renal Cell Cancer in the United States" *JAMA*, May 1999, pp. 1628-1631, vol. 281, No. 17.

Clark, J.I. et al. "Adjuvant High-Dose Bolus Interleukin-2 for Patients With High-Risk Renal Cell Carcinoma: A Cytokine Working Group Randomized Trial" *Journal of Clinical Oncology*, Aug. 15, 2003, pp. 3133-3140, vol. 21, No. 16.

Cohen, H.T. et al. "Medical Progress: Renal-Cell Carcinoma" *The New England Journal of Medicine*, Dec. 8, 2005, pp. 2477-2490, vol. 353, No. 23.

Dermer, G.B. "The Last Word: Another Anniversary for the War on Cancer" *Bio/Technology*, Mar. 1994, p. 320, vol. 12.

Dietz, J.R. et al. "Evidence supporting a physiological role for proANP-(1-30) in the regulation of renal excretion" *Am J Physiol Regul Integr Comp Physiol*, 2001, pp. R1510-R1517, vol. 280.

Freshney, R.I. "Culture of Animal Cells: A Manual of Basic Technique" Alan R. Liss, Inc.: New York, 1983, pp. 3-4.

Garrett, M.D. et al. "Discovering Novel Chemotherapeutic Drugs for the Third Millennium" *European Journal of Cancer*, 1999, pp. 2010-2030, vol. 35, No. 14.

Gunning, M.E. et al. "Atrial Natriuretic Peptide$_{(31-67)}$ Inhibits Na$^+$ Transport in Rabbit Inner Medullary Collecting Duct Cells: Role of Prostaglandin E$_2$" *Journal of Clinical Investigation*, May 1992, pp. 1411-1417, vol. 89.

Gura, T. "Cancer Models: Systems for Identifying New Drugs are Often Faulty" *Science*, Nov. 7, 1997, pp. 1041-1042, vol. 278.

Heim, J.M. et al. "Urodilatin and β-ANF: Binding Properties and Activation of Particulate Guanylate Cyclase" *Biochemical and Biophysical Research Communications*, Aug. 30, 1989, pp. 37-41, vol. 163, No. 1.

Kaiser, J. et al. "Cancer: First Pass at Cancer Genome Reveals Complex Landscape" *Science*, Sep. 8, 2006, p. 1370, vol. 313.

Krontiris, T.G. "Molecular and Cellular Biology of Cancer" In: Internal Medicine, 4th Edition, Ed. Jay Stein, Elsevier Science, 1994, pp. 699-707.

Kumar, R. et al. "Stimulation of atrial natriuretic peptide receptor/ guanylyl cyclase- A signaling pathway antagonizes the activation of protein kinase C-α in murine Leydig cells" *Biochimica et Biophysica Acta*, 1997, pp. 221-228, vol. 1356.

La Vecchia, C. et al. "Smoking and Renal Cell Carcinoma" *Cancer Research*, Sep. 1, 1990, pp. 5231-5233, vol. 50.

Linder, M.W. et al. "Pharmacogenetics: a laboratory tool for optimizing therapeutic efficiency" *Clinical Chemistry*, 1997, pp. 254-266, vol. 43, No. 2.

Martin, D.R. et al. "Three peptides from the ANF prohormone NH$_2$ are natriuretic and/or kaliuretic" *Am J Physio Renal Physiol*, Dec. 1990, pp. F1401-1408, vol. 258, abstract.

McLaughlin, J.K. et al. "A Population-Based Case-Control Study of Renal Cell Carcinoma", *J Natl Cancer Inst*, Feb. 1984, pp. 275-284, vol. 72.

Nguyen, T.D. et al. "Citrus Flavonoids Stimulate Secretion by Human Colonic T$_{84}$ Cells" *The Journal of Nutrition*, 1993, pp. 259-268, vol. 123.

Pitari, G.M. et al. "Guanylyl cyclase C agonists regulate progression through the cell cycle of human colon carcinoma cells" *PNAS*, Jul. 3, 2001, pp. 7846-7851, vol. 98, No. 14.

Rosenzweig, A. et al. "Atrial Natriuretic Factor and Related Peptide Hormones" *Annual Review of Biochemistry*, 1991, pp. 229-255, vol. 60.

Saba, S.R. et al. "Immunocytochemical Localization of Atrial Natriuretic Peptide, Vessel Dilator, Long-acting Natriuretic Peptide, and Kaliuretic Peptide in Human Pancreatic Adenocarcinomas" *Journal of Histochemistry & Cytochemistry*, 2005, pp. 989-995, vol. 53, No. 8.

Saxenhofer, H. et al. "Urodilatin: binding properties and stimulation of cGMP generation in rat kidney cells" *Am J Physiol Renal Physiol*, 1993, pp. F267-F273, vol. 264, abstract.

Schulz-Knappe, P. et al. "Isolation and Structural Analysis of "Urodilatin", a New Peptide of the Cardiodilatin-(ANP)-Family, Extracted from Human Urine" *Klinische Wochenschrift*, 1988, pp. 752-759, vol. 66.

Schwede, F. et al. "Cyclic nucleotide analogs as biochemical tools and prospective drugs" *Pharmacology & Therapeutics*, 2000, pp. 199-226, vol. 87.

Scott, D.A. et al. "The Pendred syndrome gene encodes a chloride-iodide transport protein" *Nature Genetics*, Apr. 1999, pp. 440-443, vol. 21.

Shapiro, J.A. et al. "Body Mass Index and Risk of Renal Cell Carcinoma" *Epidemiology*, Mar. 1999, pp. 188-191, vol. 10, No. 2.

Sudoh, T. et al. "C-Type Natriuretic Peptide (CNP): A New Member of Natriuretic Peptide Family Identified in Porcine Brain" *Biochemical and Biophysical Research Communications*, Apr. 30, 1990, pp. 863-870, vol. 168, No. 2.

Turner, G.A. et al. "Urine cyclic nucleotide concentrations in cancer and other conditions; cyclic GMP: a potential marker for cancer treatment" *J Clin Pathol*, 1982, pp. 800-806, vol. 35.

Valentin, J.P. et al. "Urodilatin Binds to and Activates Renal Receptors for Atrial Natriuretic Peptide" *Hypertension*, 1993, pp. 432-438, vol. 21.

Vesely, B.A. et al. "Four cardiac hormones cause cell death in 81% of human ovarian adenocarcinoma cells" *Cancer Therapy*, 2007, pp. 97-104, vol. 5, Issue A.

Vesely, D.L. et al. "Atrial Natriuretic Peptide Increases Urodilatin in the Circulation", *American Journal of Nephrology*, 1998, pp. 204-213, vol. 18, abstract.

Vesely, D.L. et al. "Atrial natriuretic peptides in pathophysiological diseases" *Cardiovascular Research*, Sep. 2001, pp. 647-658, vol. 51, No. 4.

Vesely, D.L. et al. "Atrial Natriuretic Prohormone Peptides 1-30, 31-67, and 79-98 Vasodilate the Aorta" *Biochemical and Biophysical Research Communications*, Nov. 13, 1987, pp. 1540-1548, vol. 148, No. 3.

Vesely, D.L., "Atrial Natriuretic Peptide Prohormone Gene Expression: Hormones and Diseases That Upregulate its Expression" *IUBMB Life*, 2002, pp. 153-159, vol. 53.

Vesely, D.L., "Natriuretic peptides and acute renal failure" *Am J Physiol Renal Physiol*, 2003, pp. F167-F177, vol. 285.

Villarreal, D. et al. "Hemodynamic and Renal Effects of ProANF$_{31-67\ (44399)}$, Proceedings of the Society for Experimental Biology and Medicine*, 1999, pp. 166-170, vol. 221, No. 3.

White, R.E. et al. "Potassium channel stimulation by natriuretic peptides through cGMP-dependent dephosphorylation" *Nature*, Jan. 21, 1993, pp. 263-266, vol. 361.

Wigle, D.A. et al. "ANP secretion from small cell lung cancer lines: a potential model of ANP release" *Am J Physiol Heart Circ Physiol*, 1995, pp. H1869-H1874, vol. 268, abstract.

Yagoda, A. et al. "Chemotherapy for Advanced Renal-Cell Carcinoma: 1983-1993" *Seminars in Oncology*, Feb. 1995, pp. 42-60, vol. 22, No. 1.

Yang, J.C. et al. "Randomized Study of High-Dose and Low-Dose Interleukin-2 in Patients With Metastatic-Renal Cancer" *Journal of Clinical Oncology*, Aug. 15, 2003, pp. 3127-3132, vol. 21, No. 16.

Yu, M.C. et al. "Cigarette Smoking, Obesity, Diuretic Use, and Coffee Consumption as Risk Factors for Renal Cell Carcinoma" *J Natl Cancer Inst*, Aug. 1986, pp. 351-356, vol. 77.

Zeidel, M.L., "Regulation of Collecting Duct Na$^+$ Reabsorption by ANP 31-67" *Clinical and Experimental Pharmacology and Physiology*, 1995, pp. 121-124, vol. 22, abstract.

Zellner, A. et al. "Disparity in Expression of Protein Kinase C α in Human Glioma versus Glioma-derived Primary Cell Lines: Therapeutic Implications" *Clinical Cancer Research*, Jul. 1998, pp. 1797-1802, vol. 4.

Zips, D. et al. "New Anticancer Agents: in Vitro and in Vivo Evaluation" *In Vivo*, Jan./Feb. 2005, pp. 1-7, vol. 19, No. 1.

Eichelbaum, E.J. et al. "Cardiac and kidney hormones cure up to 86% of human small-cell lung cancers in mice" *Eur J Clin Invest*, 2008, 38(8):562-570.

Lenz, A. et al. "Cardiac Hormones Eliminate some Human Squamous Lung Carcinomas in Athymic Mice" *European Journal of Clinical Investigation*, 2010 in press, p. 1-13.

Vesely, D.L. et al. "Four Cardiac Hormones Eliminate up to Two-Thirds of Human Breast Cancers in Athymic Mice" *In Vivo*, 2007, 21:973-978.

Vesely, D.L. et al. "Elimination of Up to 80% of Human Pancreatic Adenocarcinomas in Athymic Mice by Cardiac Hormones" *In Vivo*, 2007, 21:445-452.

\* cited by examiner

DENDROASPIS NATRIURETIC PEPTIDE FOR TREATMENT OF CANCER

CROSS REFERENCE TO RELATED APPLICATIONS

This application is a NonProvisional Application of copending U.S. Provisional Application No. 60/821,760, filed Aug. 8, 2006, which is incorporated herein by reference.

STATEMENT OF GOVERNMENT INTEREST

This invention was made with Government support from a merit award from the Department of Veteran Affairs. The Government has certain rights in the invention.

FIELD OF INVENTION

This invention relates to cancer therapy.

BACKGROUND OF THE INVENTION

In 2005, there were an estimated 18,500 new cases of brain tumors and estimated 12,760 deaths. Gliomas are the most common primary tumors arising from the central nervous system and of the gliomas the most common form (and the most aggressive) is glioblastoma multiforme. At present with surgery, chemotherapy and radiation the survival of the most aggressive of the primary tumors of the brain, i.e., glioblastoma multiforme (WHO grade IV) is only 50 weeks. Less than 2% of patients survive three years post diagnosis. Less than 30% of malignant gliomas respond to adjunct chemotherapy. The epidermal growth factor receptor is frequently overexpressed or mutated in glioblastomas, but only 10 to 20% respond to epidermal growth factor receptor kinase inhibitors. It is important to note in this regard that the "response" referred to above was not that the tumor was eliminated or decreased in volume but rather that the tumor did not grow more than 25%. In each of the "response" patients the glioblastomas began to grow again in approximately three months.

Cardiac natriuretic hormones are a family of peptide hormones that have significant anticancer effects on human prostate, breast, colon, and pancreatic adenocarcinoma cells (see Vesely, B. A., McAfee, Q., Gower, W. R., Jr., and Vesely, D. L. (2003) Four peptides decrease the number of human pancreatic adenocarcinoma cells. *Eur. J. Clin. Invest.* 33, 998-1005; Vesely, B. A., Alli, A. A., Song, S., Gower, W. R., Jr., Sanchez-Ramos, J., and Vesely, D. L. (2005a) Four peptide hormones specific decrease (up to 97%) of human prostate carcinoma cells. *Eur. J. Clin. Invest.* 35, 700-710; Vesely, B. A., Song, S., Sanchez-Ramos, J., Fitz, S. R., Solivan, S. M., Gower, W. R., Jr., and Vesely, D. L. (2005c) Four peptide hormones decrease the number of human breast adenocarcinoma cells. *Eur. J. Clin. Invest.* 35, 60-69; and Gower, W. R., Jr., Vesely, B. A., Alli, A. A., and Vesely, D. L. (2005) Four peptides decrease human colon adenocarcinoma cell number and DNA synthesis via guanosine 3', 5'-cyclic monophosphate. Int J Gastrointestinal Cancer 36, 77-88; which are incorporated herein by reference) as well as upon small-cell and squamous lung carcinoma cells in vitro (see Vesely B. A., Song S., Sanchez-Ramos J., Fitz S. R., Alli A. A., Solivan S. M., Gower W. R. Jr., and Vesely D. L. (2005) Five cardiac hormones decrease the number of human small-cell lung cancer cells. *Eur. J. Clin. Invest.* 35, 388-398; Vesely, B. A., Fitz, S. R., Gower, W. R., Jr., and Vesely, D. L. (2006) Vessel dilator: Most potent of the atrial natriuretic peptides in decreasing the number and DNA synthesis of squamous lung cancer cells. *Cancer Lett.* 232, 226-231, which are incorporated herein by reference).

Of this family of peptide hormones, one gene in the heart synthesizes a 126 amino acid (a.a.) prohormone which with proteolytic processing results in four peptide hormones consisting of 1) the first 30 a.a. of this prohormone (i.e., long acting natriuretic peptide, LANP), 2) vessel dilator (VDL, a.a. 31-67), 3) kaliuretic peptide (KP, a.a. 79-98), and 4) atrial natriuretic peptide (ANP, a.a. 99-126) of the 126 a.a. prohormone (FIG. 1). Vessel dilator appears to have the strongest anticancer effects decreasing up to 97% the number of human prostate and colon cancer cells within 24 hours. In vivo, vessel dilator decreases the volume of human pancreatic adenocarcinomas growing in athymic mice the most (49% decrease in tumor volume in one week), while all four peptide hormones stop the growth of this cancer in vivo. None of these cardiac hormones have ever been investigated on any tumor in the brain i.e., in the central nervous system. The four peptide hormones synthesized by the cardiac gene were evaluated for their effects on the most common of the central nervous system tumors, i.e., glioblastomas. In addition, a peptide similar to ANP has been isolated from the venom of the Green Mamba snake and termed Dendroaspis Natriuretic Peptide (DNP; see Schweitz, H., Vigne, P., Moinier, D., Frelin, C., and Lazdunski, M. (1992) A new member of the natriuretic peptide family is present in the venom of the Green Mamba (*Dendroaspis augusticeps, J. Biol. Chem.* 267, 13928-13932, which is incorporated herein by reference).

SUMMARY OF THE INVENTION

The invention includes the use of four cardiac natriuretic peptides i.e., atrial natriuretic peptide (ANP), vessel dilator, long acting natriuretic peptide (LANP), and kaliuretic peptide as well as Dendroaspis natriuretic peptide (DNP), isolated from the Green Mamba snake venom with similar structure to ANP, as anticancer agents in glioblastomas. Dose-response curves revealed a significant ($p<0.0001$) decrease in human glioblastoma cells with each ten-fold increase in concentration from 1 µM to 100 µM of four of the cardiac peptide hormones. There was an 75%, 68%, 67%, and 65% elimination within 24 hours of glioblastoma cells secondary to vessel dilator, kaliuretic peptide, ANP, and LANP, respectively ($p<0.0001$) while DNP had no significant effect at 1 µM (2% decrease), and 10 µM (7%), but 100 µM caused a (17%) decrease ($p<0.05$). Three days after treatment with these peptide hormones, the cancer cells began to proliferate again. These same hormones decreased DNA synthesis from 65% to 87% ($p<0.00001$). Western blots revealed for the first time natriuretic peptide receptors (NPR)-A, and -C were present in the glioblastoma cells. These results indicate the four cardiac hormones have potent anticancer effects by eliminating up to 75% of glioblastoma cells within 24 hours of treatment.

Therefore, in one embodiment, the invention includes a method of inhibiting the growth of cancer cells comprising the step of contacting at least one target cell with an effective amount of dendroaspis natriuretic peptide. In a preferred embodiment, the dendroaspis natriuretic peptide is administered in vivo.

In another embodiment, the invention includes a method of inhibiting the growth of cancer cells by co-administering, to at least one target cell, an effective amount of a combination of dendroaspis natriuretic peptide and a cardiac hormone. In a preferred embodiment, the cardiac hormone is selected from the group consisting of atrial natriuretic peptide, long acting natriuretic peptide, vessel dilator, and kiliuretic peptide.

BRIEF DESCRIPTION OF THE DRAWINGS

For a fuller understanding of the invention, reference should be made to the following detailed description, taken in connection with the accompanying drawings, in which:

As shown in FIG. 3, time course in decrease of human glioblastoma cell number with 100 μM concentration of atrial natriuretic peptide (▲), kaliuretic peptide (△), vessel dilator (●), and long acting natriuretic peptide (□), at 24, 48, 72, and 96 hours were significant at $p<0.001$ while Dendroaspis natriuretic peptide (■) was significant at $p<0.05$ compared to placebo-treated (○) glioblastoma cells when evaluated by repeated analysis of variance ($n=60$ for each group).

DETAILED DESCRIPTION OF THE PREFERRED EMBODIMENT

Dendroaspis natriuretic peptide (DNP), originally isolated from the venom of the *Dendroaspis angusticeps* (green mamba snake), is a 38-amino-acid peptide that contains a 17-amino-acid disulfide ring structure with 15-residue C-terminal extension. This peptide shares structural similarity to atrial natriuretic peptide (ANP), brain natriuretic peptide (BNP), and C-type natriuretic peptide (CNP). Atrial natriuretic peptide has demonstrated significant ($p<0.0001$) anticancer effects. Similarly, DNP has anticancer effects, killing up to 19% of human glioblastoma cells within 24 hours.

Figure 1:
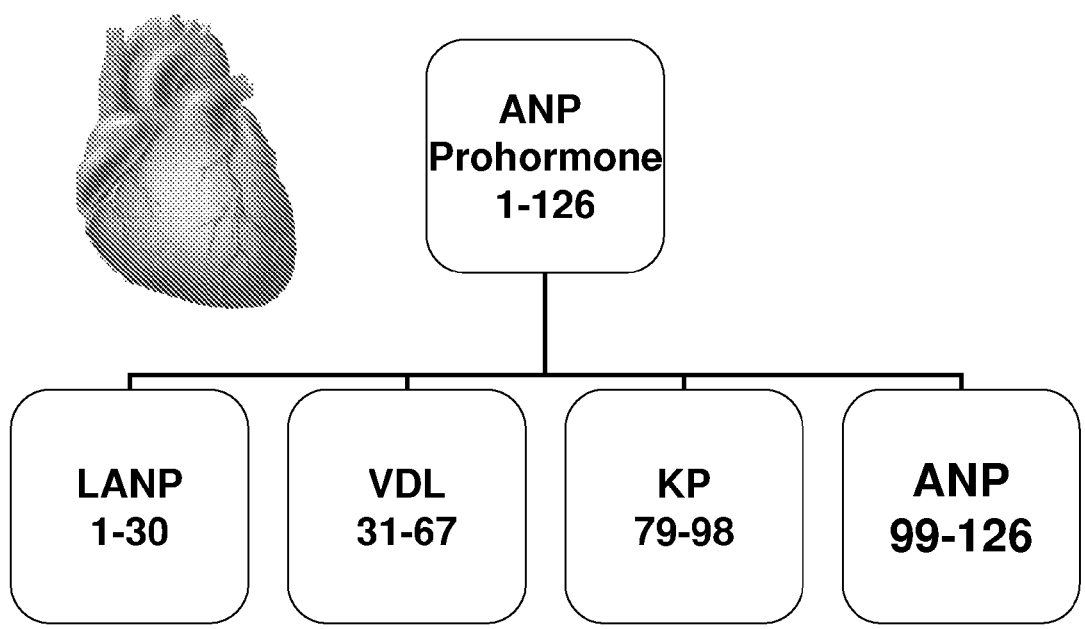
FIG. 1 is a block diagram illustrating the atrial natriuretic peptide gene in the heart which synthesizes a 126 amino acid (a.a.) prohormone with which proteolytic processing results in the formation of four cardiac hormones.

The atrial natriuretic peptide gene in the heart synthesizes a 126 amino acid (a.a.) prohormone with which proteolytic processing results in the formation of four cardiac hormones (FIG. 1). These four cardiac hormones, i.e., 1) long acting natriuretic peptide (LANP) consists of the first 30 amino acids of the 126 a.a. prohormone, 2) vessel dilator (VDL), a.a. 31-67 of the prohormone, 3) kaliuretic peptide (KP), a.a. 79-98 of this prohormone and 4) atrial natriuretic peptide (ANP), consisting of a.a. 99-126 of the 126 a.a. prohormone.

Herein, the inventors disclose for the first time that Dendroaspis natriuretic peptide (DNP) is a potential anticancer agent. DNP, isolated from the Green Mamba snake's venom, had no significant anticancer effects at is 1 μM and 10 μM concentrations where the other four peptides decreased the average number of glioblastoma cells by 37% and 53%, respectively. At 100 μM, however, DNP had anticancer effects decreasing the number of glioblastoma cells by 17% which was less ($p<0.001$) than the ability of the four cardiac peptide hormones which decreased the number of human glioblastoma cells by an average of 69% at this concentration.

This 4-fold greater ability of each of the four peptides synthesized from the cardiac gene to decrease the number of human glioblastoma cells suggests that they will have greater effects in vivo against human glioblastomas based upon these peptide hormones in vitro and in vivo effects correlating well when human pancreatic adenocarcinomas has been examined. Each of the human cardiac hormones had significant anticancer effects on human glioblastoma cells at 100-fold lower concentrations than the concentration (100 μM) where DNP first began to have an effect. DNP, however, has shown to decrease the number of glioblastoma cells and may therefore be an effective substitute for the four peptides synthesized from the cardiac gene. Alternatively, DNP is may be used as a cotreatment agent to enhance the anticancer effect of these peptides.

Figure 2:
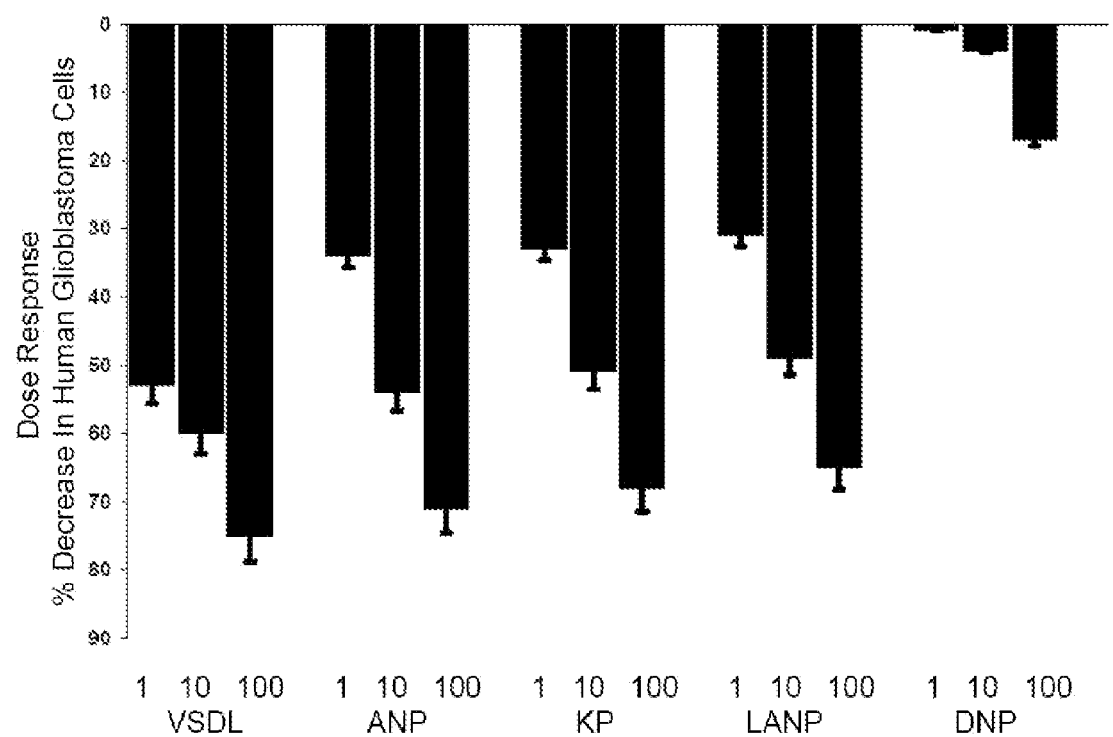
FIG. 2 shows the dose-response of kaliuretic peptide (KP), atrial natriuretic peptide (ANP), vessel dilator (VDL), long acting natriuretic peptide (LANP), and Dendropaspis natriuretic peptide (DNP) anticancer effects on human glioblastoma cells. DNP has significant effects ($p<0.05$) at its 100 μM concentration.

FIG. 2 shows the dose-response of kaliuretic peptide (KP), atrial natriuretic peptide (ANP), vessel dilator (VDL), long acting natriuretic peptide (LANP), and Dendropaspis natriuretic peptide (DNP) anticancer effects on human glioblastoma cells. As each increasing concentration of these five peptide hormones there was a significant ($p<0.05$) decrease in glioblastoma cells within 24 hours except between the 1 μM and 10 μM concentrations of vessel dilator and DNP when evaluated by repeated measures of ANOVA. Vessel dilator caused the same decrease as the other peptide hormones at a 10-fold lower concentration, as observed in this figure ($n=60$ for each group). DNP had significant effects ($p<0.05$) only at its highest concentration when evaluated by repeated measures of ANOVA.

Vessel dilator was the most potent of these peptide hormones in decreasing the number of human glioblastoma cells at each of the respective concentrations of the peptide hormones (FIG. 2). In the dose-response curves of the present investigation, when vessel dilator concentration was increased 10-fold and 100-fold (i.e., 10 μM and 100 μM), vessel dilator decreased the number of human glioblastoma cells by 60% and 75%, respectively, within 24 hours compared to 53% decrease at its 1 μM concentration (FIG. 2). Vessel dilator also decreased human pancreatic, breast, colon and prostate adenocarcinomas as well as decreasing small-cell and squamous lung cancer cells in vitro the most. This information plus the knowledge that vessel dilator decreases the tumor volume of human pancreatic adenocarcinomas the most in vivo after one week of treatment suggests that vessel dilator has the most significant anticancer properties of the five peptide hormones with anticancer effects in the present investigation. At each 10-fold increase in concentration of the respective peptide hormones in the present investigation (FIG. 2) vessel dilator's anticancer effects on human glioblastoma cells were more significant than the other four peptides ($p<0.05$).

The remaining three peptide hormones synthesized by the cardiac ANP gene, however, had significant effects on decreasing the number of human glioblastoma cells. When the concentration of kaliuretic peptide, ANP, and LANP were increased to 100 μM they caused a very significant 65%-68% decrease in the number of glioblastoma cells within 24 hours. There appears to be a difference in these peptide hormones ability to decrease cancer cell number depending on the type of cancer. Kaliuretic peptide's (1 μM), for example, ability to decrease the number of human glioblastoma cells (32% decrease) is similar to most other cancers with a 30% decrease in prostate adenocarcinoma and small-cell lung cancer cells but its effects in the present investigation are less than its effect on human pancreatic adenocarcinoma cells (37% decrease). It is important to note that after 24 hours of incubation with the five peptides that cellular debris was present, suggesting that cellular necrosis was occurring. Three days after no further exposure to these peptides the glioblastoma cells began to proliferate indicating that these peptide hormones need to be given in more than a one-day exposure if one would hope to stop the growth of glioblastomas. If, however, one gives these peptide hormones continuously to human cancer cells for four days, there is no proliferation of cancer cells. These peptide hormones' anticancer effects are at concentrations above concentrations are which they normally circulate in the human body. The circulating concentrations in healthy humans of LANP, vessel dilator, kaliuretic peptide, and ANP are 1528±158 pg/ml; 1595±157 pg/ml; 213±42 pg/ml, and 63±2 pg/ml, respectively.

Each of the four peptide hormones from the cardiac ANP prohormone inhibited 65%-84% of the amount of DNA synthesis in the human glioblastoma cells. We have previously demonstrated that the DNA synthesis-inhibiting properties of these peptide hormones synthesized by the cardiac ANP gene were directly due to the peptide hormones themselves as when their specific antibodies were incubated with the peptide hormones the antibodies completely blocked these peptide hormones ability to decrease cancer cell DNA synthesis. The antibodies by themselves did not block DNA synthesis. These findings suggest that one important mechanism of action of the five peptide hormones in the present investigation ability to inhibit cancer cell number is via their ability to inhibit DNA synthesis. The present investigation is the first evaluation of whether human glioblastoma cells or any brain tumor cells contain natriuretic peptide receptors. The NPR-A and NPR-C receptors were present in these human glioblastoma cells to help mediate ANP's and DNP's anticancer effects in the glioblastoma cells.

With an estimated 12,760 brain tumor deaths in 2005 with surgery and current cancer chemotherapy plus radiation there is an urgent need to develop new approaches to therapy of brain tumors. The present investigation details not only one but five new potential therapies, four of which kill up to 75% of human glioblastoma cells within 24 hours. The four human cardiac hormones which circulate normally in the human body have no known cytotoxic effects to normal cells and only one known side effect. This side effect, i.e., hypotension, has only been observed with ANP and never with vessel dilator, LANP, or kaliuretic peptide in human or animal subjects. Present use of chemotherapy commonly causes toxicity in the form of nausea, vomiting, alopecia, and myelosuppression. None of these toxicities occur with the cardiac natriuretic peptide hormones. The side effects of DNP isolated from the green mamba snake venom (a neurotoxin) are unknown but DNP did have anticancer effects on glioblastoma cells, although at 100-fold higher concentrations than the human cardiac hormones.

EXAMPLES

Human Glioblastoma Cells

A cell line (ATCC number CRL-11543) of human glioblastoma cells were purchased from American Type Culture Collection (ATCC, Manassas, Va.). This glioblastoma cell line was deposited by the Ludwig Institute for Cancer Research, University of California at San Diego, La Jolla, Calif. This glioblastoma cell line produces angiogensis inhibiting factor.

Culture of the Human Glioblastoma Cells

Propagation of these human glioblastoma cells was in Dulbecco's modified Eagle's medium with 4 mM L-glutamine adjusted to contain 1.5 g/L sodium bicarconate and 4.5 g/L glucose supplemented with 1 µg/ml tetracycline, 90%, and 10% fetal bovine serum (Atlanta Biologicals, Lawrenceville, Ga.) at a temperature of 37° C. in a CO2-free environment as recommended by the ATCC. Cells were dispensed in new flasks with subculturing two to three times per week.

Research Protocol

After the glioblastoma cells were subcultured for 24 hours they were then seeded to coverslips in 24-well plates (Nunclon™, Roskilde, Denmark) with 1 mL of the above media. There were 65,000 cells seeded to each coverslip. After 24 hours, the well plates were washed twice with phosphate-buffered saline to remove the fetal bovine serum. Removal of serum was carried out to completely remove all variables (EGF, etc.) present in serum in order that interpretation of any data obtained would be straightforward. After 24 hours of serum deprivation, media volume was reduced to 250 µL per well with, or without, the respective peptide hormones in dose-response curves with concentrations up to and including 100 µM (1% of this volume). Human glioblastoma cells were then incubated for various periods of time (24, 48, 72, and 96 hours). The number of glioblastoma carcinoma cells were then counted with a cell counter (Thomas Scientific, Swedesboro, N.J.) evaluating ten fields of the microscope slide at ×40 along the X-axis with an Olympus BH-2 microscope (Atlanta, Ga.). This evaluation was repeated on six separate occasions with the number of human glioblastoma cells reflecting 60 observations for each group, i.e., 60 observations for controls and 60 observations for each of the five groups with respective peptide hormones. The peptide hormones used in this investigation were from Phoenix Pharmaceuticals, Inc., Belmont, Calif. In the Results section, the number of cancer cells reported is the number of cells in each individual field. Ten fields were examined on each microscope slide. The results of the ten fields were pooled and the average of the ten fields is illustrated in the Results section.

Determination of DNA Synthesis

To investigate whether these peptide hormones were inhibiting DNA synthesis, bromodeoxyuridine (BrdU) incorporation into the human glioblastoma cells was utilized as previously described from our laboratory. BrdU was from BD Bioscience, San Jose, Calif. After 24 hours in culture with 1 µM of LANP, vessel dilator, kaliuretic peptide, ANP, and DNP, respectively, or with no peptide hormone (i.e., control), BrdU in a final concentration of 10 µM in the cell culture medium was added for 45 minutes, which is the time in which the cells are in the logarithmic phase of cell proliferation.

ANP Receptors in Human Glioblastoma Cells

Human glioblastoma cells have never been examined to determine if they have natriuretic receptors. When it was found that these cardiac peptide hormones decreased the number of human glioblastoma cells, it was then evaluated whether glioblastoma cells have ANP receptors to mediate these effects. Western blots of the natriuretic peptide receptors (NPR)-A and -C were performed as described previously from our laboratory using 75 µg of protein extract from human glioblastoma cells, measured using the bicinchoinic acid protein assay kit (Pierce; Rockford, Ill.), which was loaded onto each lane of a Criterion Precast 7.5% Tris-HCl gel (Bio-Rad; Hercules, Calif.), separated by electrophoresis (100 volts for 120 min), and then transblotted onto a nitrocellulose membrane (Hybond-C Extra, Amersham Biosciences Corporation, Piscataway, N.J.) for 75 min at 100 volts in Towbin buffer.

Statistical Evaluation

The data obtained in this investigation are illustrated as mean±SEM. Maximum changes in cell death (evaluated six times with ten areas of microscope slide evaluated each time) and DNA synthesis within groups were determined by a paired one-tailed Student's t test evaluated with statistical module of Excel software. To be considered statistically significant, we required a probability value to be <0.05 (95% confidence limits).

The number of human glioblastoma cells decreased by four peptide hormones synthesized by the cardiac ANP gene. The number of human glioblastoma cells in culture for 24 hours decreased 53%, 60% and 75% (down to 33±2 cancer cells from 130±3 cells) secondary to vessel dilator at its 1 μM, 10 μM, and 100 μM concentrations, respectively ($p<0.0001$ for each) (FIG. 2). Dose-response curves revealed that LANP in culture for 24 hours decreased the number of glioblastoma cells 31%, 49% and 65% (decreased to 43±2 cancer cells) at its 1 μM, 10 μM, and 100 μM concentrations, respectively ($p<0.001$ for each) (FIG. 2). Exposure of the human glioblastoma cells to kaliuretic peptide resulted in a 33%, 51%, and 68% decrease (43±2 glioblastoma cells) at its 1 μM, 10 μM, and 100 μM concentrations, respectively ($p<0.001$ for each) (FIG. 2). The addition of ANP decreased the number of glioblastoma cells in 24 hours by 30%, 52% and 67% at its 1 M, 10 μM, and 100 μM concentrations. Thus, with respect to their ability to inhibit the growth of human glioblastoma cells when these cells were exposed to identical 100 μM concentrations of these peptide hormones for 24 hours was vessel dilator>kaliuretic peptide>ANP>LANP. When the number of glioblastoma cells was examined immediately after the incubation with the respective peptide hormones, there was no decrease in the number of glioblastoma cells. In the wells with a decreased number of glioblastoma cells secondary to the cardiac hormones there was evidence of cellular debris.

Figure 3:
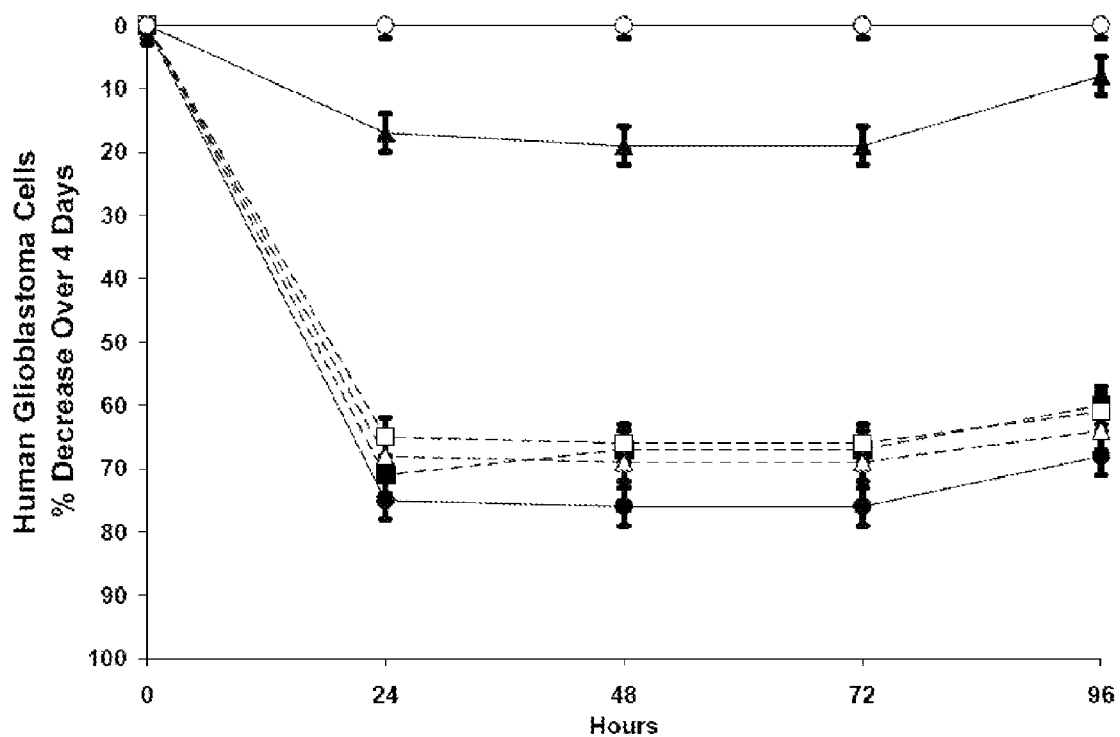
FIG. 3 is a graph demonstrating decreased glioblastoma proliferation for four days after initial 24 hour exposure of these peptide hormones.

When the glioblastoma cells were followed for three days after treatment with vessel dilator, LANP, kaliuretic peptide and ANP there was nearly complete inhibition of proliferation of glioblastoma cells at 48 and 72 hours after the decrease in the number of the glioblastoma cells at 24 hours by the peptide hormones from the cardiac ANP prohormone gene (FIG. 3). As shown in FIG. 3, time course in decrease of human glioblastoma cell number with 100 μM concentration of atrial natriuretic peptide (▲), kaliuretic peptide (Δ), vessel dilator (●), and long acting natriuretic peptide (□), at 24, 48, 72, and 96 hours were significant at $p<0.001$ while Dendroaspis natriuretic peptide (■) was significant at $p<0.05$ compared to placebo-treated (○) glioblastoma cells when evaluated by repeated analysis of variance (n=60 for each group).

Thus, when exposed to vessel dilator for 24 hours but without exposure to vessel dilator for the next 24 hours, the decrease in number of human glioblastoma cells at 48 hours was 76%, 60%, and 53% at 100 μM, 10 μM, and 1 μM of vessel dilator (non-significant difference from the amount of decrease at 24 hours). Likewise at 48 hours the decrease in glioblastoma cells secondary to kaliuretic peptide was nearly identical to that observed at 24 hours with a 68%, 51%, and 32% decrease at 48 hours with 100 μM, 10 μM, and 1 μM of kaliuretic peptide (non-significant difference from 24 hours). At 48 hours, after an exposure to LANP for only 24 hours, there was a 65%, 50%, and 31% decrease in glioblastoma cell number at its 100 μM, 10 μM and 1 μM concentrations. Exposure to ANP for 24 hours but without exposure ANP for the next 24 hours resulted in no proliferation of glioblastoma cells as there was a 67%, 52%, and 30% decrease in glioblastoma cells with 100 μM, 10 μM, and 1 μM of ANP (non-significant difference comparing these different concentrations 24 hours and 48 hours). Two days after exposure to the respective peptide hormones (i.e., 72 hours in FIG. 3 illustrated for 100 μM concentration) there was no proliferation in the remaining glioblastoma cells. Thus, with vessel dilator there was an 76%, 60% and 53% decrease while with kaliuretic peptide there was a 68%, 52%, and 32% decrease at 72 hours in human glioblastoma cells at their 100 μM, 10 μM, and 1 μM concentrations, respectively. LANP caused a 66%, 50%, and 31% decrease while with ANP there was a 67%, 52% and 31% decrease in glioblastoma cancer numbers at their 100 μM, 10 μM, and 1 μM concentrations at 72 hours.

Three days after exposure to the respective peptide hormones, there was some proliferation of the glioblastoma cells (FIG. 3). Thus, the glioblastoma cells that had not been exposed to vessel dilator for three days had a 68%, 55%, and 43% decrease in cancer cell number compared to control and with kaliuretic peptide there was a 64%, 40%, and 25% decrease and the decreases secondary to LANP and ANP were 61%, 39%, 24% and 60%, 43% and 24% at their 100 μM, 10 μM, and 1 μM concentrations, respectively. This is an aggressive cancer cell in culture as evidenced by the control number of glioblastoma cells increasing 77%, 180%, and 280% at 48, 72 and 96 hours compared to 24 hours.

Dendroaspis natriuretic peptide (DNP)'s anticancer properties were much less significant than the four peptide hormones from the ANP gene. Thus, at 24 hours DNP decreased the number of human glioblastoma cells 2% (n.s.), 7% (n.s.) and 17% ($p<0.05$) at its 1 μM, 10 μM, and 100 μM concentrations. Likewise, at 48 hours, DNP's anticancer effects were much less potent than the four peptide hormones from the ANP gene causing a 1% (n.s.), 7% (n.s.) and 19% decrease ($p<0.05$), while at 72 hours there was a 1% (n.s.), 6% (n.s.) and 19% decrease ($p<0.05$) in the number of human glioblastoma cells. Three days (i.e. at 96 hours) after the exposure to DNP for 24 hours there was a 1% (n.s.), 5% (n.s.), and 8% (n.s.) decrease in the number of glioblastoma cells. DNP's anticancer effects only became significant when it was utilized in a 100-fold higher concentration than the human cardiac hormones.

To help determine the mechanism of glioblastoma cells' decrease in number and cellular proliferation by the above five hormones, the present study investigated if their effects were owing to an inhibition of DNA synthesis.

Figure 4:
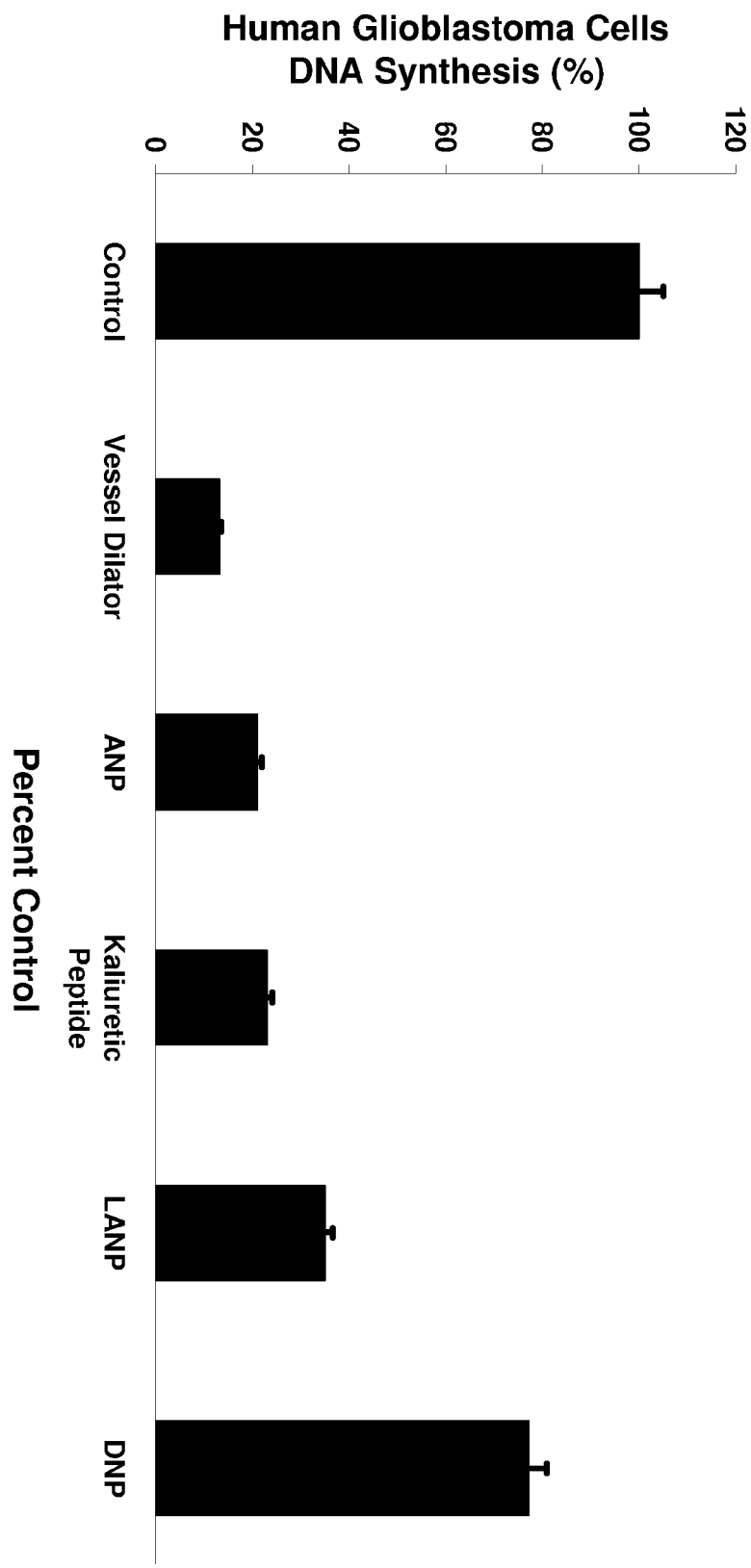
FIG. 4 is a graph showing the decrease in DNA synthesis by Dendroaspis natriuretic peptide (DNP), atrial natriuretic peptide (ANP), kaliuretic peptide, vessel dilator, and long acting natriuretic peptide (LANP).

The decrease in DNA synthesis by Dendroaspis natriuretic peptide (DNP), atrial natriuretic peptide (ANP), kaliuretic peptide, vessel dilator, and long acting natriuretic peptide (LANP) are shown in FIG. 4. The 65 to 84% decrease in DNA synthesis secondary to the four cardiac hormones hormones each at 1 μM, was significant ($p<0.001$) compared to control (i.e., untreated) cells while BNP and DNP's effects were not significant (23% decrease) when evaluated by repeated measures of analysis of variance (ANOVA) (n=30 for each group).

Vessel dilator, LANP, kaliuretic peptide and ANP each at their 1 μM concentrations inhibited DNA synthesis when incubated with the human glioblastoma cells for 24 hours by 87%, 65%, 77%, and 79%, respectively ($p<0.001$ for each) (FIG. 4). DNP decreased DNA synthesis 23% (n.s.).

Figure 5:
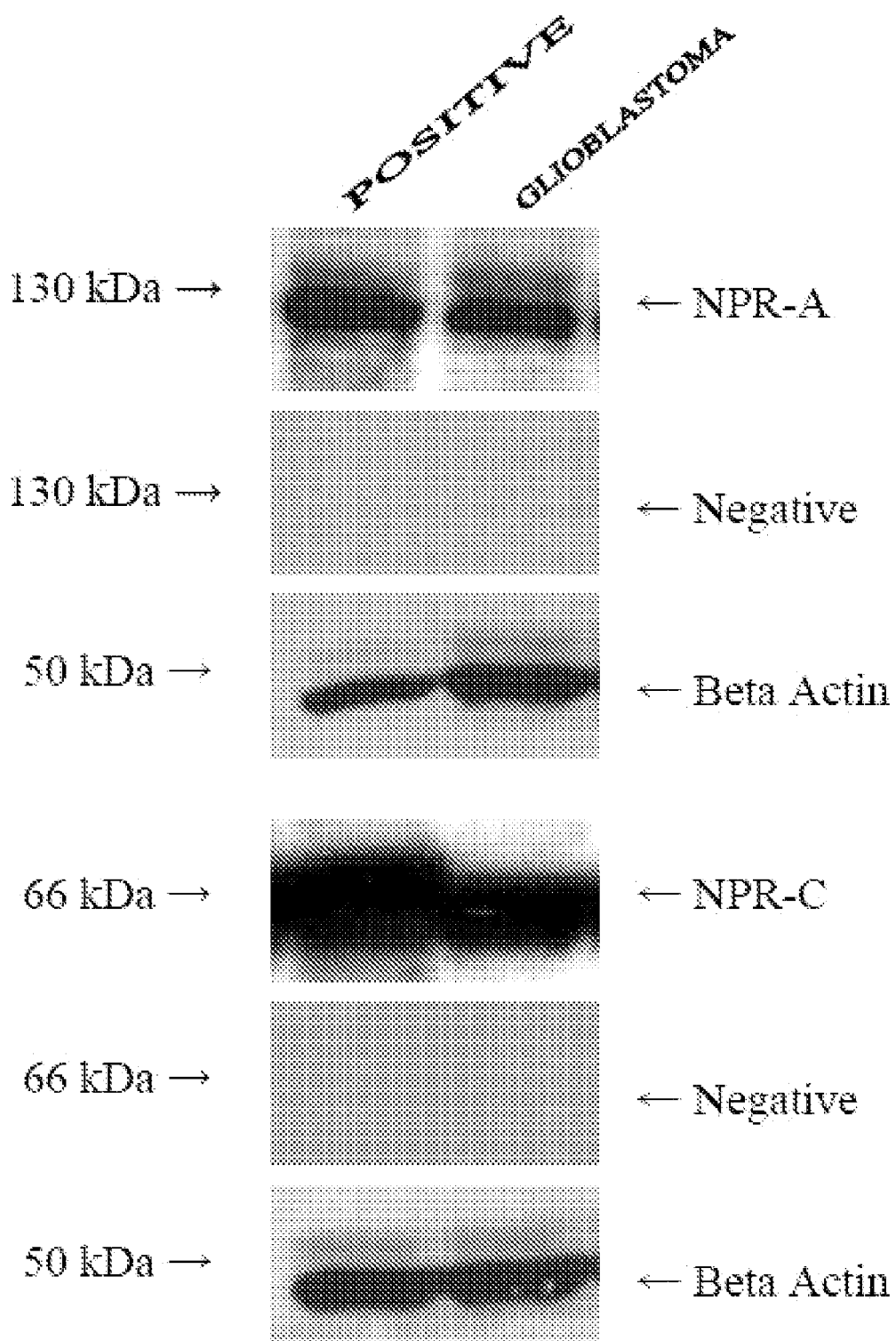
FIG. 5 is a series of Western blots showing natriuretic peptide receptors (NPR)-A, and -C are present in human glioblastoma cells.

Glioblastoma cells have never been evaluated to determine whether they have NPR-A and/or -C receptors. When the human glioblastoma cells were evaluated by Western blots, the NPR-A and -C receptors were demonstrated to be present (FIG. 5).

Natriuretic peptide receptors (NPR)-A, and -C are present in human glioblastoma cells. Western blot analysis with a 1:4000 dilution of R1214 polyclonal antibody directed against the COOH terminus of the natriuretic peptide A-receptor (kindly provided by Dr. David L. Garbers, University of Texas Southwestern, Dallas, Tex.) and a 1:1000 dilution of Omori antibody to the NPR-C receptor (generously provided by Dr. Kenji Omori, Osaka, Japan). The left side blots are the positive controls for each of the receptors. The NPR-A receptor in human glioblastoma cells is in the upper panel at 130 Kilo Dalton (kDa). The lower panel blot demonstrates the NPR-C receptor at 66 kDa in the human glioblastoma cells. The negative controls are in the right panel of this figure. Albumin (bovine serum albumin, BSA) (70 kDa) was used in addition to BIO RAD Precision Plus Protein Dual Color standards to identify the bands corresponding to the NPR-A and -C receptors, respectively. Re-probing with actin was used as a loading control. The glioblastoma cells for receptor analysis were scraped from 100 mm dishes in ice cold mammalian protein extraction reagent (M-PER; Pierce; Rockford, Ill.) containing Halt™ phosphatase inhibitor (Pierce) and Halt™ protease inhibitor (Pierce).

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pa., Mack Publishing Company, 19th ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question. The pharmaceutical composition can be adapted for various forms of administration. Administration can be continuous or at distinct intervals as can be determined by a person skilled in the art.

The administration of DNP and/or the ANP prohormone compounds are administered and dosed in accordance with good medical practice, taking into account the clinical condition of the individual patient, the site and method of administration, scheduling of administration, patient age, sex, body weight, and other factors known to medical practitioners.

The pharmaceutically "effective amount" for purposes herein is thus determined by such considerations as are known in the art.

A therapeutically effective amount of each respective peptide, or any combination thereof, is that amount necessary to provide a therapeutically effect. The amount of peptide must be effective to achieve a response. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of inhibiting the growth of cancer cells, comprising the step of contacting at least one target cancer cell with an effective amount of dendroaspis natriuretic peptide.

2. The method of claim 1, wherein the target cancer cell is a glioblastoma cell.

3. The method of claim 1, wherein the dendroaspis natriuretic peptide is administered in vivo.

4. The method of claim 3, wherein the target cancer cell is a human cell.

5. The method of claim 3, wherein the target cancer cell is a pancreatic adenocarcinoma cell, breast adenocarcinoma cell, colon adenocarcinoma cell, or prostate adenocarcinoma cell.

6. The method of claim 1, wherein the target cancer cell is a human cell.

7. The method of claim 6, wherein the target cancer cell is a pancreatic adenocarcinoma cell, breast adenocarcinoma cell, colon adenocarcinoma cell, or prostate adenocarcinoma cell.

8. The method of claim 1, wherein the target cancer cell is a pancreatic adenocarcinoma cell, breast adenocarcinoma cell, colon adenocarcinoma cell, or prostate adenocarcinoma cell.

9. A method of inhibiting the growth of cancer cells comprising the step of co-administering, to at least one target cancer cell, an effective amount of a combination of dendroaspis natriuretic peptide and a peptide selected from the group consisting of atrial natriuretic peptide, long acting natriuretic peptide, vessel dilator, and kaliuretic peptide.

10. The method of claim 9, wherein the effective amount of the combination of peptide hormones is administered in vivo.

11. The method of claim 10, wherein the target cancer cell is a human cell.

12. The method of claim 10, wherein the target cancer cell is a pancreatic adenocarcinoma cell, breast adenocarcinoma cell, colon adenocarcinoma cell, or prostate adenocarcinoma cell.

13. The method of claim 9, wherein the target cancer cell is a human cell.

14. The method of claim 9, wherein the target cancer cell is a pancreatic adenocarcinoma cell, breast adenocarcinoma cell, colon adenocarcinoma cell, or prostate adenocarcinoma cell.

15. A method of inhibiting the growth of cancer cells, comprising the step of contacting at least one target cancer cell with an effective amount of a mixture comprising dendroaspis natriuretic peptide and a peptide selected from the group consisting of atrial natriuretic peptide, long acting natriuretic peptide, vessel dilator, and kaliuretic peptide.

16. The method of claim 15, wherein the target cancer cell is a human cell.

17. The method of claim 15, wherein the target cancer cell is a pancreatic adenocarcinoma cell, breast adenocarcinoma cell, colon adenocarcinoma cell, or prostate adenocarcinoma cell.

* * * * *

UNITED STATES PATENT AND TRADEMARK OFFICE
CERTIFICATE OF CORRECTION

| | | |
|---|---|---|
| PATENT NO. | : 7,825,092 B2 | |
| APPLICATION NO. | : 11/833757 | |
| DATED | : November 2, 2010 | |
| INVENTOR(S) | : David L. Vesely | |

It is certified that error appears in the above-identified patent and that said Letters Patent is hereby corrected as shown below:

On the Title Page
Lines 2-3 of item (73), "United States Department of Veteran Affairs,"
    should read --United States Department of Veterans Affairs,--.

Column 1,
Lines 9-17, "which is incorporated herein by reference.

STATEMENT OF GOVERNMENT INTEREST
    This invention was made with Government support from a merit award from the Department of Veteran Affairs. The Government has certain rights in the invention.

FIELD OF INVENTION" should read

--which is incorporated herein by reference.

FIELD OF INVENTION--.

Column 2,
Line 66, "kiliuretic" should read --kaliuretic--.

Column 3,
Lines 12-13, "Dendropaspis natriuretic peptide" should read
    --Dendroaspis natriuretic peptide--.
Line 60, "effects at is 1 µM" should read --effects at 1 µM--.

Column 4,
Lines 13-14, "DNP is may be used" should read --DNP may be used--.
Lines 18-19, "Dendropaspis natriuretic peptide" should read
    --Dendroaspis natriuretic peptide--.

Signed and Sealed this
Fifth Day of April, 2011

David J. Kappos
*Director of the United States Patent and Trademark Office*

Column 5,
Line 9, "above concentrations are which they" should read
 --above the concentrations at which they--.
Lines 25-26, "peptide hormones in the present investigation ability"
 should read --peptide hormones in their ability--.
Line 26, "is via their ability" should read --is their ability--.
Line 58, "were purchased" should read --was purchased--.
Line 67, "sodium bicarconate" should read --sodium bicarbonate--.

Column 7,
Line 25, "1 M" should read --1 µM--.

Column 8,
Lines 48-49, "cardiac hormones hormones each" should read --cardiac hormones each--.